US 6,788,977 B2
(12) United States Patent
Fenn et al.

(10) Patent No.: US 6,788,977 B2
(45) Date of Patent: Sep. 7, 2004

(54) SYSTEM AND METHOD FOR HEATING THE PROSTATE GLAND TO TREAT AND PREVENT THE GROWTH AND SPREAD OF PROSTATE TUMOR

(75) Inventors: Alan J. Fenn, Wayland, MA (US); John Mon, Silver Spring, MD (US)

(73) Assignee: Celsion Corporation, Columbia, MD (US)

( * ) Notice: Subject to any disclaimer, the term of this patent is extended or adjusted under 35 U.S.C. 154(b) by 22 days.

(21) Appl. No.: 10/247,747

(22) Filed: Sep. 20, 2002

(65) Prior Publication Data

US 2003/0069619 A1 Apr. 10, 2003

Related U.S. Application Data

(63) Continuation-in-part of application No. 09/597,234, filed on Jun. 20, 2000, now Pat. No. 6,477,426.

(51) Int. Cl.[7] .................................................. A61F 2/00

(52) U.S. Cl. ..................... 607/101; 607/102; 606/15; 601/2

(58) Field of Search ................................. 607/101–102, 607/96, 98, 99; 606/13–15, 17, 18; 601/2; 424/450

(56) References Cited

U.S. PATENT DOCUMENTS

| | | | |
|---|---|---|---|
| 3,895,639 A | | 7/1975 | Rodler |
| 4,589,423 A | | 5/1986 | Turner |
| 4,813,429 A | | 3/1989 | Eshel et al. |
| 5,007,437 A | | 4/1991 | Sterzer |
| 5,207,672 A | * | 5/1993 | Roth et al. ............... 606/10 |
| 5,233,994 A | * | 8/1993 | Shmulewitz ............. 600/454 |
| 5,251,645 A | | 10/1993 | Fenn |
| 5,441,532 A | | 8/1995 | Fenn |
| 5,496,271 A | * | 3/1996 | Burton et al. ............ 607/27 |
| 5,540,737 A | | 7/1996 | Fenn |
| 5,810,888 A | | 9/1998 | Fenn |

(List continued on next page.)

FOREIGN PATENT DOCUMENTS

| | | |
|---|---|---|
| WO | WO 93/08876 A1 | 5/1993 |
| WO | WO 93/09845 A1 | 5/1993 |
| WO | WO 99/58194 A1 | 11/1999 |

OTHER PUBLICATIONS

England et al., "Dielectric Properties of the Human Body in the Microwave Region of the Spectrum", Nature, vol. 163, pp. 487–488, Mar. 26, 1949.

Duck, "Physical Properties of Tissue, A Comprehensive Reference Book", Academic Press Inc., San Diego, CA, pp. 320–321, 1990.

(List continued on next page.)

Primary Examiner—Roy D. Gibson
(74) Attorney, Agent, or Firm—Venable LLP; Catherine M. Voorhees

(57) ABSTRACT

Improvements in safety and efficacy for externally focused adaptive phased array microwave thermotherapy (hyperthermia) for treatment of cancer and benign conditions of an organ or an appendage are described. In order to reduce blood flow thereby accumulating additional equivalent thermal dose following the step of heating an organ or appendage by irradiating microwaves at the organ or appendage, the step of compressing the organ or appendage following the heating step is added to thermotherapy treatment. In a preferred embodiment, the organ is the prostate and periodic prostate compression is employed to reduce the prostate blood flow thereby allowing chemotherapy, thermosensitive liposome-encapsulated chemotherapy, or gene therapy to accumulate in the prostate region during thermotherapy. Doppler ultrasound imaging may be used to measure tumor blood flow rate and then serve as real-time feedback to assist in adjusting the amount of balloon catheter inflation and to assess damage to the tumor vasculature during the treatment.

20 Claims, 4 Drawing Sheets

U.S. PATENT DOCUMENTS

| | | | | |
|---|---|---|---|---|
| 5,860,929 A | * | 1/1999 | Rubin et al. | 600/454 |
| 5,992,419 A | | 11/1999 | Sterzer et al. | |
| 6,071,534 A | * | 6/2000 | Kim et al. | 424/450 |
| 6,123,083 A | * | 9/2000 | McGrath et al. | 128/898 |
| 6,197,309 B1 | * | 3/2001 | Wheeler | 424/727 |
| 6,200,573 B1 | * | 3/2001 | Locke | 424/727 |
| 6,200,598 B1 | | 3/2001 | Needham | |
| 6,413,544 B1 | * | 7/2002 | Smyth-Templeton et al. | 424/450 |
| 6,567,705 B1 | | 5/2003 | Stokes et al. | |

OTHER PUBLICATIONS

Foster et al., "Dielectric Properties of Tumor and Normal Tissues at Radio through Microwave Frequencies", Journal of Microwave Power, 16(2), pp. 107–119, 1981.

Valdagni, M.D. et al., "Report of Long–term Follow–up in a Randomized Trial Comparing Radiation Therapy and Radiation Therapy Plus Hyperthermia to Metastatic Lymphnodes in Stage IV Head and Neck Patients", Int. J. Radiation Oncology Biol. Phys., vol. 28, No. 1, pp. 163–169, 1993.

Overgaard et al., "Hyperthermia as an Adjuvant to Radiation Therapy of Recurrent or Metastatic Malignant Melanoma. A Multicentre Randomized Trial by the European Society for Hyperthermic Oncology", Int. J. Hyperthermia, vol. 12, No. 1, pp. 3–20, 1996.

Hall, "Radiobiology for the Radiologist", J.B. Lippincott Company, Philadelphia, pp. 262–263, 1994.

Perez et al., "Principles and Practice of Radiation Oncology", J.B. Lippincott Company, Philadelphia, second edition, pp. 396–397, 1994.

Sapareto et al., "Thermal Dose Determination in Cancer Therapy", Int. J. Radiation Oncology Biol. Phys., vol. 10, No. 6, pp. 787–800, Jun. 1984.

von Hippel et al., "Dielectric Analysis of Biomaterials", Massachusetts Institute of Technology, pp. ai–ii, and 1–20, Oct. 1973.

Bassen et al., "Evaluation of an Implantable Electric–Field Probe within Finite Simulated Tissues", American Geophysical Union, vol. 12, No. 6(s), pp. 15–25, Nov.–Dec. 1977.

Samaras et al., "Production of Controlled Hyperthermal Fields for Cancer Therapy", Urban & Schwarzenberg, pp. 131–133, 1978.

Surowiec et al., "Sar Characteristics of a Dual Intracavitary Applicator for Prostate Treatment", Hyperthermia Oncology 1992, vol. 1, p. 268, 1992.

Yeh et al., "Multiple Microwave Antenna System for Prostate Cancer Hyperthermia", Hyperthermia Oncology 1992, vol. 1, pp. 269, 1992.

Camart et al., "Rectal and Urethral Applicator Association for Prostatic Gland Microwave Thermotherapy: Modelling and Experimental Results", Hyperthermic Oncology 1996, vol. 2, pp. 598–600, 1996.

Brawer, "Prostate–Specific Antigen: Current Status", CA Cancer J. Clin. 1999, vol. 49, pp–264–281, 1991.

Oesterling, "Prostate Specific Antigen: A Critical Assessment of the Most Useful Tumor Marker For Adenocarcinoma of the Prostate", The Journal of Urology, vol. 145, pp. 907–923, May 1991.

Zagars, M.D. et al., "The Prognostic Importance of Gleason Grade in Prostatic Adenocarcinoma: A Long–term Follow–up Study of 648 Patients Treated with Radiation Therapy", Int. J. Radiation Oncology Biol. Phys., vol. 31, No. 2, pp. 237–245, 1995.

Schröder et al., "Prostatic Cancer Detection at Low Prostate Specific Antigen", J. Urol. 2000, vol. 163, p. 806, Mar. 2000.

Eschenbach, MD et al., American Cancer Society Guideline for the Early Detection of Prostate Cancer: Update 1997, CA Cancer J. Clin. 1997, vol. 47, pp. 261–264.

Heynick, "Radiofrequency Electromagnetic Fields (RFEMF) and Cancer: A Comprehensive Review of the Literature Pertinent to Air Force Operations", Air Force Research Laboratory (AFSC) Human Effectiveness Directorate Directed Energy Bioeffects Division, Jun. 1999.

Field et al., "An Introduction to the Practical Aspects and Clinical Hyperthermia" Tayor & Francis, pp. 263, 290, 1990.

Fenn et al., "Minimally Invasive Molopole Phased Arrays For Hyperthermia Treatment Of Breast Carcinomas: Design And Phantom Tests", Presented at the 1994 International Symposium of Eclectromagnetic Compatibility, pp. 566–569, May 17–19, 1994.

Vitrogan, "Elements on Electric and Magnetic Circuits", Rinehart Press, pp. 31–34, 1971.

Gentili et al., "Two–Element Radiating System for Endocavitary Hypertermia",Hyperthermic Oncology 1988, vol. 1, pp. 904–905, Aug. 29–Sep. 3, 1988.

Barry et al., "The Ameerican Urological Association Symptom Index for Benign Prostatic Hyperplasia", vol. 148, pp. 1549–1557, Nov. 1992.

Vernon et al., "Radiotherapy with or without Hyperthermia in the Treatment of Superficial Localized Breast Cancer: Results from Five Randomized Controlled Trials", Int. J. Radiation Oncology Biol. Phys., vol. 35, No. 4, pp. 731–744, 1996.

* cited by examiner

SYSTEM AND METHOD FOR HEATING THE PROSTATE GLAND TO TREAT AND PREVENT THE GROWTH AND SPREAD OF PROSTATE TUMOR

CROSS REFERENCE TO RELATED APPLICATION

This application is a continuation-in-part of U.S. patent application Ser. No. 09/597,234, filed Jun. 20, 2000 now U.S. Pat. No. 6,477,426.

BACKGROUND OF THE INVENTION

1. Field of the Invention

The present invention generally relates to a system for administering focused energy to a body selectively using either a single energy applicator or multiple microwave applicators in order to treat visable tumors and microscopic malignant and benign cells in prostate tissue with hyperthermia. The system according to the invention may be used to treat healthy tissue containing undetected microscopic pathologically altered cells (neoplasia) that are of high-water content to prevent the occurrence of or the recurrence of cancerous, pre-cancerous or benign prostatic lesions. In addition, the disclosed system and method for using the system can prevent the growth of tumors inside the prostate, as well as prevent the spread of cancer cells outside the prostate.

2. Description of the Prior Art

In order to treat prostate tumors with hyperthermia, it is necessary to heat a significant portion of the prostate gland while sparing healthy tissues in the prostate as well as the surrounding tissues including the urethral and rectal walls of a patient. In the United States there are approximately 200,000 cases of detected prostate cancer annually as well as 375,000 cases of benign prostatic hyperplasia, known as BPH, (enlarged prostate gland). BPH is a non-cancerous enlargement (tumor) of the prostate gland that occurs in almost all men as they age, particularly past the age of 50 years. In the case of BPH, the enlargement of the prostate involves the excessive growth of tissue that eventually obstructs the bladder outlet, creating difficulties with urination. In the case of prostate cancer, eventually the cancer will break through the prostate gland capsule leading to the spread of cancer to the bones and vital organs of the body. Although some of the signs of BPH and prostate cancer are the same, having BPH does not increase the chances of getting prostate cancer. Nevertheless, a patient who has BPH may have undetected prostate cancer at the same time or may develop prostate cancer in the future.

As is known in the art, the use of heat to treat prostate tumors can be effective in a number of ways; however, in most cases, the heat treatment must be capable of heating a significant volume of the prostate gland without overheating the urethral and rectal walls. In radiation therapy, the entire prostate and adjacent tissues are irradiated with x-rays to kill all the microscopic cancer cells. While heating large volumes of the prostate can destroy many or all of the microscopic carcinoma cells in the prostate, known methods of heating tumors can destroy healthy tissue in the prostate and, more damaging, in the urethral and rectal walls of a patient.

The prostate gland has electrical properties similar to muscle (T. S. England and N. A. Sharples, Nature, Vol. 163, Mar. 26, 1949, pp. 487–488.) and is known to have a high-water content, on the order of 80% (F. A. Duck, Physical Properties of Tissue, A Comprehensive Reference Book, Academic Press, New York, p. 321, 1990). Tumor tissue, in general, tends to be 10 to 20% higher in water content than normal tissue (Foster and Schepps, Journal of Microwave Power, vol. 16, number 2, pp. 107–119, 1991). Thus, prostate tumors may have a water content on the order of about 90%. Accordingly, selective microwave heating of the prostate would be the best method of targeting cancerous or benign cells.

It is well known that microwave energy can heat high-water content tumor tissues faster when compared to the heating that occurs in lower-water content normal tissues. Tumor tissue tends to be poorly perfused so blood flow often decreases at therapeutic temperatures allowing rapid heating, while in normal tissues the blood flow often increases protecting the normal healthy tissue from heat damage. Many clinical studies have established that hyperthermia (elevated temperature) induced by electromagnetic energy absorption in the microwave band, significantly enhances the effect of radiation therapy in the treatment of malignant tumors in the human body (Valdagni, et al., International Journal of Radiation Oncology Biology Physics, Vol. 28, pp. 163–169, 1993; Overgaard et al., International Journal of Hyperthermia, Vol. 12, No. 1, pp. 3–20, 1996; Vernon et al., International Journal of Radiation Oncology Biology Physics, Vol. 35, pp. 731–744, 1996). Radio-resistant cells such as S-phase cells can be killed directly by elevated temperature (Hall, Radiobiology for the Radiologist, $4^{th}$ Edition, JB Lippincott Company, Philadelphia, pp. 262–263, 1994; Perez and Brady, Principles and Practice of Radiation Oncology, Second Edition, JB Lippincott Company, Philadelphia, pp. 396–397, 1994). Hyperthermia treatments with microwave radiating devices are usually administered in several treatment sessions, in which the malignant tumor is heated to about 43° C. for about 60 minutes. It is known that the amount of time to kill tumor cells decreases by a factor of two for each degree increase in temperature above about 43° C. (Sapareto, et al., International Journal of Radiation Oncology Biology Physics, Vol. 10, pp. 787–800, 1984). Thus, a 60-minute heat-alone treatment at 43° C. can be reduced to only about 15 minutes at 45° C., which is often referred to as an equivalent dose ($t_{43}$° C. equivalent minutes).

During treatments with noninvasive microwave applicators, it has proven difficult to heat semi-deep tumors adequately while preventing surrounding superficial healthy tissues from incurring pain or damage due to undesired hot spots. The specific absorption rate (SAR) in tissue is a common parameter used to characterize the heating of tissue. The SAR is proportional to the rise in temperature over a given time interval times the specific heat of the tissue, and for microwave energy the SAR is also proportional to the electric field squared times the tissue electrical conductivity. The units of absolute SAR are watts per kilogram.

The first published report describing a non-adaptive phased array for deep tissue hyperthermia was a theoretical study (von Hippel, et al., Massachusetts Institute of Technology, Laboratory for Insulation Research, Technical Report 13, AD-769-843, pp. 16–19, 1973). U.S. Pat. No. 3,895,639 to Rodler describes two-channel and four-channel non-adaptive phased array hyperthermia circuits. Likewise, a non-adaptive phased array hyperthermia system was disclosed in U.S. Pat. No. 4,589,423 to Turner.

Bassen et al., Radio Science, Vol. 12, No. 6(5), November–December 1977, pp. 15–25, shows that an electric-field probe can be used to measure the electric-field pattern in tissue, and in particular, shows several examples in which the measured electric-field has a focal peak in the central tissue. This paper also discusses a concept for real-time measurements of the electric field in living specimens. However, Bassen et al. did not develop the concept of measuring an electric field using real-time with an electric-probe to adaptively focus a phased array.

The most difficult aspect of implementing hyperthermia in deep prostatic tissues, with microwave energy, is producing sufficient heating at a predetermined depth while protecting the urethral and rectal walls and surrounding organs from burns. Noninvasive multiple applicator adaptive microwave phased arrays with invasive and noninvasive electric field probes can be used for producing an adaptively focused beam at the tumor position with adaptive nulls formed in healthy tissues as described in U.S. Pat Nos. 5,251,645, 5,441,532, 5,540,737, and 5,810,888 to Fenn, all of which are incorporated herein by reference. Ideally, a focused microwave radiation beam is concentrated at the tumor with minimal energy delivered to surrounding healthy tissue. To control the microwave power during treatment, a temperature-sensing feedback probe (Samaras et al., Proceedings of the $2^{nd}$ International Symposium, Essen, Germany, Jun. 2–4, 1977, Urban & Schwarzenberg, Baltimore, 1978, pp. 131–133) is inserted into the tumor, however, it is often difficult to accurately place the probe in the tumor. An additional difficulty occurs in delivering hyperthermia to carcinoma spread throughout the prostate gland, because of a lack of a well-defined target position for the temperature-sensing feedback probe. In other situations, it is desirable simply to avoid inserting probes (either temperature or E-field) into the prostate tissue in order to reduce the risk of infection or spreading the cancer cells when the probe passes through the tumor region.

Several articles have been written on the use of dual intracavitary (transurethral and transrectal) coherent phased array microwave applicators for prostate cancer treatment (A. Surowiec, et al., Hyperthermic Oncology 1992, Vol. 1, Summary Papers, Proceedings of the $6^{th}$ International Congress on Hyperthermic Oncology, Apr. 27–May 1, 1992 (Arizona Board of Regents), p. 268 (abstract); M. M. Yeh, et. al. Hyperthermic Oncology 1992, Vol. 1, Summary Papers, Proceedings of the $6^{th}$ International Congress on Hyperthermic Oncology, Apr. 27–May 1, 1992 (Arizona Board of Regents), p. 269 (abstract); and J. C. Camart, Hyperthermic Oncology 1996, Vol. 2, Proceedings of the $7^{th}$ International Congress on Hyperthermic Oncology, Rome, Italy, Apr. 9–13, 1996, pp. 598–600). Further, U.S. Pat. No. 5,007,437 to Sterzer describes the use of non-coherent transurethral and transrectal applicators for BPH treatments. However, the known prior art is directed to the use of transurethral and transrectal applicators for treating solid tumor masses. None of the known procedures are concerned with treating microscopic disease and preventing the occurrence of solid tumor masses such that occur in cancer and BPH.

Prostate Cancer

The current standard of medical care for treating prostate cancer includes radical or nerve-sparing prostatectomy in which the entire prostate gland is surgically removed, and brachytherapy in which radiation seeds at low dose are permanently implanted in the prostate gland radiating effectively for 6 to 9 months or radiation seeds at high dose are temporarily implanted in the prostate for about 2 days, combined with external-beam radiation therapy to catch microscopic cancer cells that may have penetrated or could penetrate the prostate capsule. Side effects from surgery include incontinence and impotence. The cancer recurrence rate after surgery can be as high as approximately 35% at 5 years, and approximately 60% at 10 years, particularly when the prostatic-specific antigen level (discussed below) is greater than 10. Radiation therapy has short-term side effects such as skin reactions, fatigue and nausea. Additional long-term side effects of radiation therapy to the prostate include urinary incontinence (loss of bladder control) and impotence, as well as damage to surrounding organs.

Hormone therapy is also used to supplement prostate cancer treatments by stopping cancer cells from growing. Male hormones, such as testosterone, help cancer cells grow and, in contrast, female hormones or estrogens inhibit growth. Side effects of estrogen therapy include nausea and vomiting, hot flashes, fluid retention, weight gain, headaches and gynecomastia (an increase in breast tissue) in men.

Fundamentally, the problem with current prostate treatments is the inability to control microscopic capsule penetration from the prostate gland, which spreads the cancer to vital organs. Men with microscopic capsule penetration of cancer cells are not cured by radical prostatectomy. These microscopic cells may spread far from the prostate gland into vital organs by means of the lymphatic system or by blood vessels through the prostate capsule.

It is possible to detect the presence of prostate cancer by means of the well-known serum assay Prostate-Specific Antigen (PSA) test (M. K Brawer, "Prostate-Specific Antigen: Current Status," CA A Cancer Journal for Clinicians, Vol. 49, pp. 264–281, 1999, and J. E. Oesterling, "Prostate Specific Antigen: A Critical Assessment of the Most Useful Tumor Marker for Adenocarcinoma of the Prostate," The Journal of Urology, Vol. 145, pp. 907–923, May 1991.). The prostatic lumen contains the highest concentration of PSA in the human body. PSA is an enzyme produced in all types of prostatic tissue (normal, benign hyperplastic and malignant). In particular, PSA is a serine protease that is produced only by the epithelial cells lining the acini and ducts of the prostate gland; none of the other cellular components of the prostate, including the stromal and vascular elements produce PSA. Researchers have verified that PSA is produced in the epithelial cells of BPH tissue, primary prostate cancer tissue, and metastatic prostate cancer tissue. The serum PSA test detects a significant number of prostate cancers and the destruction of prostatic tumors leads to reduced PSA levels, since the body stops producing PSA when the tumors are eliminated. Currently, a PSA level of 4.0 ng/ml or greater is used to decide whether a patient will be biopsied to try to verify the presence of carcinoma in the prostate. Thus, patients with a PSA level under 4.0 ng/ml currently are not biopsied even if they experience the signs and symptoms of prostate cancer which may include: frequent urination, especially at night, inability to urinate, trouble starting or holding back urination, a weak or interrupted urine flow and frequent pain or stiffness in the lower back, hips or upper thighs.

In addition to PSA level, the Gleason Grade is used to histologically grade adenocarcinoma of the prostate (G. K. Zagars, et al, International Journal of Radiation Oncology Biology Physics, Vol. 31, No. 2, pp. 237–245, 1995), with Grade 1 being the least malignant and slowest growing. Gleason Grade 3 is the most commonly occurring grade when diagnosed. Gleason Grades 4, 5 and above (up to 10) are considered highly aggressive, rapidly growing carcinomas.

Biopsy results and staging are used to predict the behavior of the cancer and the likelihood of its spread. Stage 1 tumors are small and cannot be felt on rectal examination. Stage 2 or greater refers to prostates in which the tumor can be felt. Stage 3 cancers have spread beyond the boarders of the prostate. In Stage 4, which can be determined by imaging studies such as bone scans, CT, or MRI scans, the cancer has spread into nearby lymph glands, the bones, or elsewhere in the body. As is well known in the medical field, the earlier the cancer is detected, the better the chance of being a cancer survivor. If detection is not possible before stage 2, the next best medical option would be to safely treat apparently healthy tissue. Thus, there is a need to treat healthy tissue since cancer, in general, cannot be detected until it has reached stage 2 or a later stage.

There are four types of prostate ductal carcinomas: transitional cell carcinoma, intraductal adenocarcinoma, mixed ductal carcinoma, and endometrioid carcinoma. Transitional cell and mixed ductal carcinomas are aggressive cancers that require complete removal of the prostate and bladder if found while the tumor is still confined to the prostate. Complete removal of the prostate and bladder is also the medically accepted treatment for endometrioid carcinoma. Intraductal adenocarcinomas are treated by radical prostatectomy. Thus, there is a need for a system for treating and preventing the growth and spread of cancer that does not require surgical prostatectomy.

Benign Prostatic Hyperplasia

Benign Prostatic Hyperplasia (BPH) is described primarily as an enlargement of the prostate gland that exerts pressure on the urethra, resulting in obstruction of the flow of urine, and is a common affliction in middle-aged and older males. Approximately 50% of men older than 65 years will have BPH symptoms that significantly affect their quality of life. The American Urological Association (AUA) Symptom Index was developed to help categorize BPH symptoms. The AUA score has the following score ranges: 0 to 7 points—BPH symptoms are considered mild; 8 to 19 points—BPH symptoms are considered moderate; and 20 to 35 points—BPH symptoms are considered severe. However, many BPH patients do not seek treatment until their AUA score is about 12.

Over the last two decades, a number of treatments for BPH have been developed each with advantages and disadvantages. The major types of BPH treatment systems are: 1) transurethral resection of the prostate (TURP), 2) Transurethral Electrovaporization of the Prostate (TVP), 3) Drugs, 4) Interstitial Laser Coagulation, 5) RF Needle Ablation, and 6) Microwave Thermotherapy of the Prostate. Other treatment techniques have been explored, including transurethral incision of the prostate, prostatic stents, and balloon dilation, but are used to a lesser extent.

BPH treatment success and practicality can measured in terms of 1) efficacy, 2) durability, 3) level of pain (during and after the procedure), 4) recovery period, 5) complexity of the procedure, 6) cost of the procedure, and 7) side effects. Efficacy of BPH treatments is commonly quantified using the AUA Symptom Index (SI) and peak urine flow rate. Normal urine flow rate is about 16 ml/sec. Other optional tests such as residual urine volume and pressure flow are sometimes used to judge efficacy. Durability is the length of time for which the treatment is effective. The level of pain relates primarily to the need for either general anesthesia or local anesthesia. The recovery period is measured in terms of the number of days of hospitalization and home rest. The complexity of the procedure is a function of the length of the procedure, the training of the individual administering the procedure (either an urologist or a technician), the type of anesthesia required, and the length of time needed for Foley catheterization after treatment. The cost of the procedure is influenced strongly by the length and complexity of the procedure—particularly whether a hospital stay is required.

Until about 1990, the major treatment ("Gold Standard") for BPH was Transurethral Resection of the Prostate (TURP) which is administered by urologists. TURP is expensive, requires a long recovery time, and has a number of significant side effects, which has prompted the search for better treatment techniques. A summary of approaches to treat BPH, including surgery, drug and laser, RF, and microwave applications is described below.

Transurethral Resection of the Prostate (TURP)

The "Gold Standard" of BPH treatments involves a surgical procedure in which a rigid transurethral scope with an electrosurgical loop is used to remove part of the enlarged prostate tissue (primarily the central zone of the prostate) with RF energy. In practice, 90% of surgical procedures for BPH involve TURP, due to its excellent efficacy (85% or more), long-term durability (10 to 15 years) for 90% of patients. On the order of 200,000 TURPs are performed in the United States annually. TURP has a number of drawbacks: It is a very painful procedure and requires both 2–4 days of hospitalization and 2–4 weeks of recovery at home. The TURP procedure is performed in about one hour and requires general anesthesia. An urologist must perform the procedure. A Foley catheter is required for about 2–3 days post treatment. Some of the major potential side effects of a TULRP include impotence, incontinence, high blood loss, and retrograde ejaculation.

Open Prostatectomy

An open prostatectomy is primarily used on patients with very large prostates with excellent results: the efficacy is greater than 95% and the durability is the same as TURP (10 to 15 years). With any surgical procedure, the pain level is very high and general anesthesia is required. About 7 to 10 days of hospitalization is required with an additional 3–5 weeks spent at home. The procedure takes a few hours and must be performed by a urologist. Following the treatment, a Foley catheter must be used for 2–4 days to drain the bladder. An open prostatectomy is about twice the cost of a TURP, and has the serious potential side effects and complications including high blood loss, impotence, and incontinence.

Transurethral Electrovaporization of the Prostate (TVP)

Basically a modification of TURP, transurethral electrovaporization of the prostate employs a grooved electrosurgical rollerball electrode to channel open the urethra that is blocked by the prostate tissue. The TVP procedure is safer and has minimal side effects compared to TURP. The efficacy is excellent (85%), but still is a very painful procedure requiring 2–4 days of hospitalization and 1–2 weeks at home. A urologist performs this 60-minute procedure and the patient is under a general anesthetic. A Foley catheter must be used for 2–4 days following this procedure. The procedure costs slightly less than TURP. There is less blood loss than with TURP, but their are still the potential side effects of impotence, incontinence, and retrograde ejaculation.

Transurethral Incision of the Prostate (TUIP)

In a relatively new procedure for patients with small prostates, transurethral incision of the prostate provides an efficacy of about 80%. However, TUIP is not effective on large prostates. A minimal amount of prostate tissue is removed in this procedure—a simple incision is made along the entire length of the prostate. The TUIP procedure allows the bladder neck to spring open, allowing free urinary flow. The durability is expected to be similar to TURP, but clinical research is still in progress. This procedure is moderately painful and requires only a day or two of hospitalization, or for some patients is an outpatient procedure. Usually, 4 to 7 days of home rest are needed following the procedure. A urologist must perform this 60-minute surgical procedure and a Foley catheter must be used for 2 to 4 days. The cost of the TUIP is about the same as TURP. There is less blood loss with this procedure compared to TURP, but there are still the potential side effects of impotence, incontinence, and retrograde ejaculation.

Balloon Dilation

For patients with small prostates, balloon dilation within the prostatic urethra can be used to offer some relief from BPH symptoms. The efficacy is only about 60% and the durability is only 1 to 5 years. This procedure is less costly than TURP and is usually performed as an outpatient with several days of home rest. The procedure is performed under local anesthesia by a urologist in about 30 minutes. A Foley catheter is required for about 2–4 days. There may be some bleeding in this procedure and there are the possible side effects of infection and impotence. The procedure does not work well on large prostates.

Stents

For very ill patients with small prostates, stents can be used with good effectiveness to improve BPH symptoms. Durability is not a major issue since these patients are usually very ill with other diseases. This procedure is moderately painful and requires only local anesthesia, is performed in about 30-minutes by a urologist, and is done as an outpatient with about 4–5 days of home rest. The cost of this procedure is less costly than TURP. Some of the potential side effects are irritation, infection, and the formation of debris on the stent.

Drugs

Two categories of drugs are used in treating BPH. One category uses an alpha blocker (Hytrin or Cardura) to relax the muscles that surround the prostate to allow better urinary flow. The other type of drug is reductase inhibitor (Proscar) which actually shrinks the prostate gland. Hytrin, for example, has very good efficacy (74%) and offers some immediate relief of BPH symptoms, however 2–3 weeks are needed until the full effectiveness is reached. Clinical data suggests that this drug has at least 3 to 5 years durability and is simply prescribed by a general practitioner. The cost is less than TURP depending on the number of years of treatment. There can be some serious side effects such as dizziness, chest pain, irregular heartbeat, and shortness of breath.

Proscar works well on large prostates, but is ineffective on small prostates. Full effectiveness of the drug takes about 3 to 6 months and the durability is estimated at least 3 to 5 years. This drug is prescribed by a general practitioner and must be taken for at least 12 months. The cost of the drug is less than TURP. Some of the known side effects are impotence, swollen lips, decreased volume of ejaculate, and skin rash.

Interstitial Laser Coagulation

Here, an interstitial laser coagulation surgical device delivers laser energy radially along the length of a custom-designed light diffuser. The diffuser produces an ellipsoidal pattern of thermal damage, applying the laser energy omnidirectionally and uniformly, to maximize treated tissue volume in the prostate. This is a moderately painful surgical procedure, requiring one or two days in the hospital and then 1 to 2 weeks at home. This 30-minute procedure must be performed by a urologist, with a choice of either general or local anesthesia depending on the patient's condition. A serious disadvantage with this procedure is the lengthy required time of 1 to 2 weeks in which a Foley catheter must be used to drain the bladder of urine. The cost of the procedure is less than TURP. There are many potential side effects from this treatment including impotence, incontinence, blood loss, and retrograde ejaculation.

RF Needle Ablation (Transurethral Needle Ablation)

This system uses two high-energy RF (approximately 0.47 MHz) needles that are inserted through the urethra into the prostate, to ablate the prostate tissue in a few minutes. More than 10,000 patients worldwide have been treated with this system, which provides good to very good efficacy. There is only limited 12-month durability data for this system, so the long-term effectiveness is not known. The procedure is moderately painful (local anesthesia required) and is performed as an outpatient with 1–2 weeks for home recovery. The procedure is usually performed by a urologist in about 30 minutes. About 40% of patients will require a Foley catheter for about 2 to 3 days. The procedure costs less than TURP. The major side effects from this procedure are irritating voiding, erectile dysfunction, and retrograde ejaculation.

In view of the known treatments for BPH, which require costly, painful, surgery or drugs which have potentially dangerous side effects, there is a need for a system of treating benign prostatic hyperplasia (BPH) that is not painful; can be accomplished on an outpatient basis; and quickly restores the patient to his normal functions. In addition, a method is needed that can safely treat the prostrate gland with focussed energy before a significant amount of microscopic tumor cells form in the prostate.

SUMMARY OF THE INVENTION

The above problems associated with known treatments are solved by the system and method for using the system according to the invention. The system and method according to the invention safely heat pre-cancerous, cancerous, pre-benign, and benign conditions of the prostate by heating the prostate gland with focussed or concentrated energy, such as microwave energy, delivered by either phase non-coherent or coherent array applicators in the urethra and rectum, or with interstitial applicators positioned within the prostate. In a non-coherent array, separate microwave oscillators can drive the applicators and there is no common phase relation. In a phase coherent array (phased array), a single microwave oscillator can drive multiple applicators with a common phase relation.

The Applicants' approach is to treat the prostate gland with focussed energy, such as microwave energy before a significant amount of microscopic tumor cells form in the prostate gland. As described above, all past uses of thermal therapy were used for the treatment of established prostate cancers with moderate to high PSA levels (over 4.0 ng/ml) or for the treatment of moderate to severe AUA symptom index scores for BPH. The preferred embodiment of this invention is for the prevention or before detection, or before medical intervention is required. Thus, the inventive method is for treating prostate cancer when the PSA level is less than 4.0 ng/ml, or for treating BPH where BPH symptoms are less than severe or the AUA symptom index score is less than 13. In other words, the inventive method is to prevent the cancer or BPH from developing into a significant problem for a patient (i.e., before serious adverse effects occur).

The preferred method of treating a prostate, according to the invention, is with a coherent adaptive phased array and comprises the steps of monitoring temperatures of walls of the urethra and rectum, orienting two microwave applicators in at least one of the urethra and rectum, adjusting the microwave power to be delivered to the prostate based on the monitored urethral and rectal wall temperatures, monitoring the microwave energy dose delivered to the prostate being treated and automatically completing the treatment when a desired total microwave energy dose has been delivered by the microwave applicators.

Incoherent-array or non-adaptive phased array hyperthermia treatment systems can be used to heat semi-deep and deep tissue, depending on the radiating frequency. Due to the dielectric heating of high-water content tissue such as prostate tumor, it may be possible to safely heat prostate tumors with either non-coherent arrays or non-adaptive phased arrays.

Moreover, the system and method according to the invention have application in situations where there is no well-defined position to place the temperature feedback sensor, or where it is desirable to avoid inserting a temperature probe into the prostate tissue. In the case of a single applicator, an E-field probe (or E-field sensors) is not necessary and thus, an invasive probe is not required in the preferred system and method according to the invention. The inventive system and method may destroy all of the prostate pre-cancerous and cancerous cells or benign lesions with heat generated by the focussed energy thereby avoiding further progression of the cancer cells or benign lesions.

In addition, the method according to the invention can be used to enhance radiation therapy or for targeted drug delivery and/or targeted gene therapy delivery with or without thermosensitive liposomes as described in U.S. Pat. No. 5,810,888 to Fenn.

The method according to the invention destroys the pre-cancerous, cancerous, pre-benign, and benign cells in the prostate while preserving normal prostate tissue. Thus, the system and method according to the invention achieves a thermal prostatectomy and avoids damage to healthy tissue. Accordingly, the inventive method is a prostate conservation technique.

The urethral and rectal wall temperature can be measured by temperature probe sensors positioned away from the transurethral and transrectal applicators to obtain the true temperature of the urethral and rectal walls. Alternatively, the tissue temperatures can be monitored by external means, including infrared, laser, ultrasound, electrical impedance tomography, magnetic resonance imaging, and radiometry techniques as known in the art.

Alternatively, a temperature probe could be inserted at an appropriate depth in the prostate tissue to monitor the temperature thereof. As discussed below, insertion of a temperature probe is not a preferred embodiment.

In an embodiment with two or more energy applicators, an invasive E-field probe, inserted in the prostate, may or may not be used to measure the microwave power delivered to the tissue to be treated to determine the length of the focussed energy treatment. In a preferred embodiment, the invasive E-field probe can be used to focus the applied energy at the E-field probe inserted in the prostate.

As an alternate embodiment, for a coherent phased array, two E-field sensors can be placed in the prostatic urethra and rectum non-invasively and be used to null the E-field in the urethra and rectum and effectively focus the microwave radiation in the prostate tissue. Additionally, the microwave phase for the transurethral and transrectal applicators can be adjusted so that the microwave energy is scanned across an area of the prostate.

The system and method according to the invention can be achieved with or without compression of the prostate. In a preferred method, a patient's prostate would be compressed by expanding at least one of a urethral balloon and a rectal balloon. Focussed energy and prostate compression provide preferential heating of high-water content prostate carcinoma and benign cells in the prostate compared to the surrounding lower-water content normal prostate tissues and tissue surrounding the prostate.

To coherently focus the energy, such as microwave energy, in the prostate, the patient's prostate can be compressed via a urethral and rectal balloon and means for determining where to focus the energy in the patient's prostate is used. The means for determining where to focus the energy can be either a single electric-field probe, inserted in the central portion of the prostate, or two noninvasive electric-field sensors on the urethral and rectal walls. The probe or sensors receive signals that can be used to measure a feedback signal in order to adjust the energy phase delivered to the applicators located in the urethra and in the rectum.

In accordance with another embodiment of the invention, the step of compressing the prostate may be maintained following the completion of the microwave-induced heating step. That is, the compression of the prostate is maintained for a period of time following the microwave-induced heating step to reduce prostate blood flow and to accumulate additional equivalent thermal dose. The prostate compression can be achieved by maintaining the inflated pressure of balloon catheters in at least one of the urethral and rectal areas. Periodic prostate compression to reduce prostate blood flow may be employed in accumulating chemotherapy, thermosensitive liposome-encapsulated chemotherapy, or gene therapy in the prostate region during thermotherapy.

The major advantages offered by treatment according to the system and method of the invention over known treatments are listed below:

1. Prevention and destruction of prostate tumors (including cancerous and benign);
2. Immediate relief from any BPH symptoms that might exist;
3. Long term durability;
4. Only low level pain may be experienced;
5. Outpatient procedure;
6. Local anesthesia;
7. No Foley catheter required; and
8. No significant side effects or complications.

A biological stent can be formed in the prostatic urethra due to the combination of compression balloon dilation and microwave heat (microwave urethroplasty) as evidenced in clinical tests held by the assignee, Celsion Corporation, during 1999. As a result, one of the major deficiencies in known BPH treatments, namely the need for a Foley catheter for several days, is no longer needed and a patient may experience immediate relief from BPH symptoms.

As described below, applicants' inventive system and method involves monitoring the microwave energy dose delivered to the prostate being treated and completing the treatment based on the total microwave energy dose that has been received. That is, conventional temperature feedback measurements of tumor thermal dose can be replaced with the total microwave energy delivered to the coherent phased array or non-coherent microwave applicators and then to the treated area Accordingly, with the instant invention, instead of temperature feedback measurements, which require the insertion of a temperature feedback probe into the prostate and its inherent problems, microwave energy dose is used as a feedback to determine the required length of treatment. In this application the term "microwave energy dose" (in Joules or watt-seconds) is similar to the dose used in radiation therapy, namely the radiation absorbed dose (Rad) which is a unit of absorbed dose of radiation defined as deposition of 100 ergs of energy per gram of tissue.

Thus, the instant method for selectively heating cancerous and benign conditions of the prostate avoids the risk of spreading cancer cells since the temperature probe is not inserted into the treated area (tumor bed) of the prostate. The elimination of an inserted temperature probe reduces the risk of infection to a patient as a result of the inserted probe. Likewise, the microwave field applied to a tumor would not be subjected to scattering or other disturbance caused by a temperature probe, especially a metallic probe. In addition, the time and costs associated with inserting the temperature probe are saved.

The inventive system and method may also be used to treat healthy prostate tissue or undetected high-water content microscopic pre-cancerous or pre-benign cells in seemingly healthy prostate tissue to prevent the occurrence of or recurrence of cancerous conditions of the prostate. Thus, the system and method according to the invention would be able to destroy or ablate microscopic precancerous or pre-benign cells in the prostate gland that are higher .in water content (e.g., 90%) than the prostate gland (e.g., 80%) before they are detected. This would be an early treatment that could prevent cancer from growing in the prostate and spreading from the prostate, or enlargement of the prostate gland. In the case of seemingly healthy tissue, the prostate tissue would be irradiated with microwave energy focused at high-water content microscopic cells that are known to form lesions without damaging the healthy lower-water content prostate tissue.

If both transurethral and transrectal applicators are used and both are expanded by respective balloons, a preferred system having means for compressing and immobilizing the prostate to reduce the tissue penetration depth and to reduce the prostate blood flow is achieved.

In an alternate method, the prostate is compressed with a single transurethral balloon, which immobilizes the prostate tissue, reduces blood flow, and reduces the penetration depth required for the microwave radiation. The compression balloon is made of a microwave transparent plastic material such as Latex. The placement of an E-field feedback probe in the prostate may be achieved with an ultrasound transducer or other type of image guidance. Further reduction in blood flow can be achieved, in a preferred method, by injecting a local anaesthetic lidocaine with ephinephrine or anti-angiogenesis drug in the prostate.

Two microwave applicators (such as described by U.S. Pat. No. 5,007,437 to Sterzer which is incorporated herein by reference) can be positioned transurethrally and transrectally. A phased array can be achieved with a multiple number of applicators greater than or equal to two. In a preferred embodiment, coherent 915 MHz microwave power is delivered to the two transurethral and transrectal applicators, at a predetermined power level, while phase shifters in each channel are adjusted to maximize and focus the microwave energy at the E-field probe sensor. Water-cooling within the catheters and balloons allows cooling of the urethral and rectal walls. Additional interstitial applicators can be inserted within the prostate to supplement the heating that is produced by the transurethral and transrectal applicators.

During the hyperthermia treatment, the microwave power level delivered to each of the applicators may be adjusted either manually or automatically to avoid high temperatures that could cause burns or blisters to the urethral or rectal walls. In addition, the amount of prostate compression, if used, is adjusted as necessary during treatment to provide patient comfort. Each time the prostate compression is adjusted, the microwave-energy/phased array is refocused so that the E-field probe sensor receives maximum power. The total microwave energy, since the start of the treatment, delivered to the microwave applicators is monitored during the treatment. The treatment is completed when a desired amount of total microwave energy is delivered to the microwave applicators, which indicates that the lesion cells are significantly destroyed (i.e., thermal downsizing) or completely destroyed (i.e., thermal prostatectomy).

In order to determine the effectiveness of the treatment, the prostate tissue may be imaged and examined with one of x-ray, ultrasound, and magnetic resonance imaging before and after the microwave total energy dose is administered, as well as with pathological results from needle biopsy of the prostate tissues.

In an alternate embodiment of the invention, the single invasive E-field probe is replaced with two E-field sensors positioned in the urethra and rectum and the coherent array is phase focused by minimizing (nulling) the individual or combined power received by the two sensors, providing a completely noninvasive treatment. In a preferred embodiment, the two E-field sensors are contained with catheters attached to the outside surface of a compression balloon which provides a pressure contact to the urethal and rectal walls. Algorithms are used in conjunction with the feedback signals sensed by the E-field sensors to null areas on the urethral and rectal walls outside thereby focussing the applied energy on an internal site. After the nulling algorithm is completed, the E-field sensors can be withdrawn and temperature sensors can be inserted to measure the urethal and rectal wall temperatures.

Such a totally non-invasive hyperthermia treatment where E-field sensors and temperature sensors monitor the urethral and rectal walls would provide an effective method of destroying benign and cancerous lesions in the prostate. In an embodiment with non-coherent applicators, an E-field focussing probe and phase shifters are not required to heat the tissue. With non-coherent energy, only the applicator radiated power is additive and phase shift is not used.

While the preferred embodiment is described with reference to adaptive microwave phased array technology, Applicants' system and method may be achieved by focussing energy, in general, to heat and ablate an area of tissue. The focused energy may include electromagnetic waves, ultrasound waves or waves at radio frequency. That is, applicants' inventive system and method includes any energy that can be focused to heat and ablate an area of tissue. This energy, such as microwave or ultrasound energy, can be coherent or non-coherent. In another embodiment, the energy may come from a fluid or a laser applicator.

In yet another embodiment of the invention with a coherent phased array, the boundary of an area of tissue to be treated in a body (e.g., prostate) is calculated, an E-field probe may be inserted in the body or at least two E-field sensors are positioned within the urethra and rectum; and energy is applied through applicators to the area to be treated. In this embodiment, the focus of the energy would change so that the focus scans the area to be treated. That is, there is no longer a fixed focus spot as the relative phase of the applied energy would be adjusted so that the focus moves inside the area to be treated thereby obtaining a geometric shape of heating.

A fixed focus spot is determined through the appropriate algorithm. Then, for example, the relative phase of the applicators to obtain this fixed focus spot is adjusted 30° one way (positive) and then 30° the other way (negative) to "scan" a larger heated/treated area. Depending on the size of the area to be treated the scan may focus between 180° and 90° or 60° or 120°.

Further objectives and advantages will become apparent from a consideration of the description and drawings.

BRIEF DESCRIPTION OF THE DRAWINGS

The invention is better understood by reading the following detailed description with reference to the accompanying figures, in which like reference numerals refer to like elements throughout, and in which.

DETAILED DESCRIPTION OF THE EMBODIMENT

Figure 1:
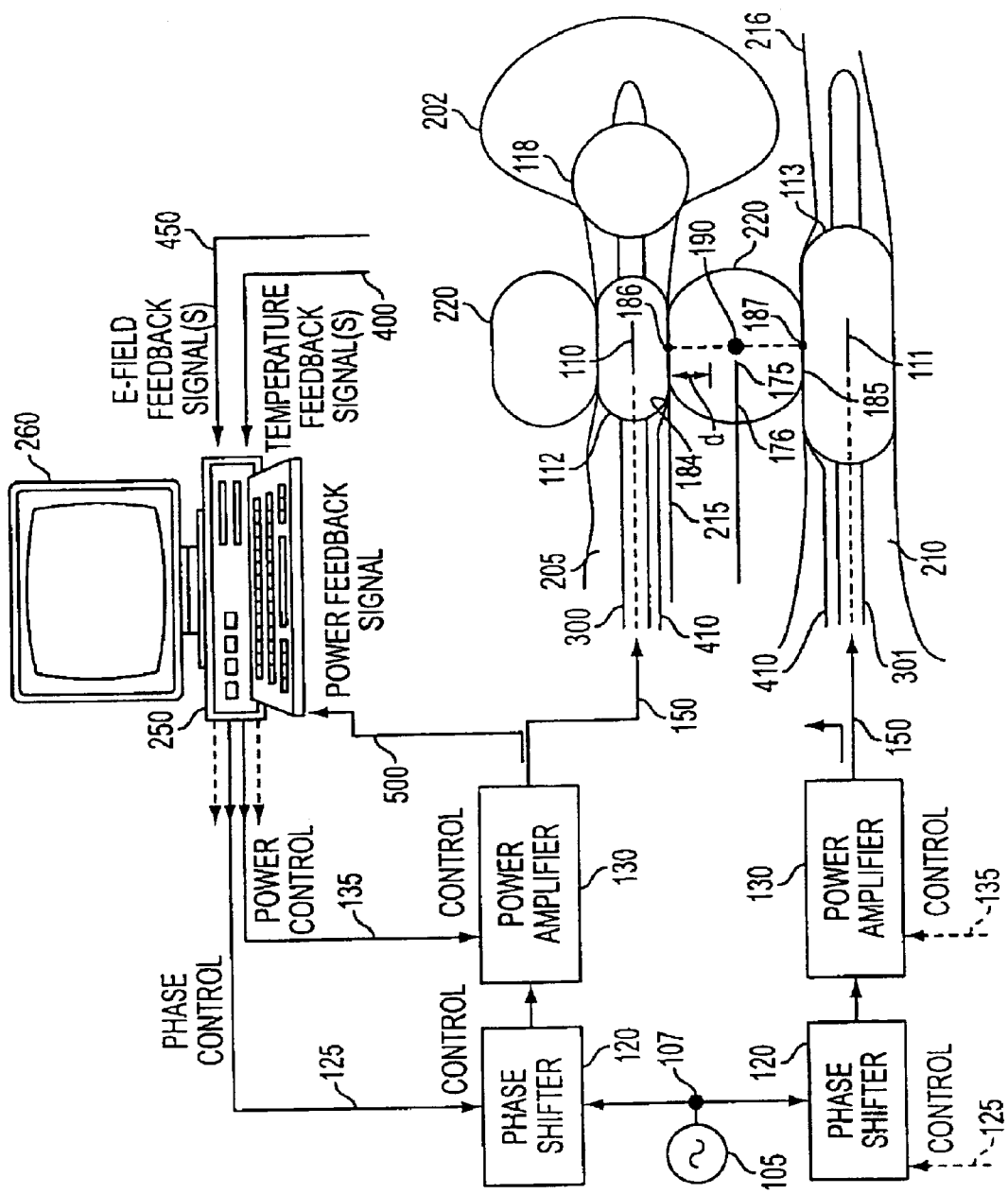
FIG. 1 shows the microwave thermotherapy system according to the invention for heating the prostate under compression from coherent transurethral and transrectal applicators.

Description of the Prostate Gland and its Microwave Properties

The prostate gland 220 is part of the male reproductive system and is a solid, walnut-shaped organ that surrounds the first part of the urethra 205 immediately under the bladder 202 and in front of the rectum 210. Prostate cancer arises from the glands of the prostate and the most common form of prostate cancer is known as adenocarcinoma, which means a cancer of the glands. Most prostate cancers develop within the bottom portion of the prostate (sometimes referred to as the peripheral zone which involves roughly 70% of the glandular prostate) closest to the rectum, and this is the region that needs a significant amount of treatment. While a digital rectal exam is useful in detecting hardened areas or lumps in the prostate gland, however it is not very useful for detecting microscopic prostate disease. The use of a transrectal applicator (in addition to a transurethral applicator) to reach this portion of the prostate is essential for a complete treatment of the prostate. The central zone of the prostate (closest to the bladder) is relatively immune to both BPH and prostate cancer diseases. BPH arises mainly in the transition zone located between the central zone and peripheral zone.

As discussed above, current medical procedure does not biopsy a tumor until a PSA of 4.0 ng/ml is reached. The data shown in Table 1 indicate that there is only about a 15% probability of detecting cancer by needle biopsy when the PSA is less than 4 ng/ml. Although the probability of detecting the cancer is very low, the actual probability that there are microscopic cancer cells in the prostate is significant (25% or more) (F. H. Schröder et. al, The Journal of Urology, Vol. 163, No. 3, p. 806 (abstract), March 2000) (Eschenbach et al., CA Cancer J. Clinicians, Vol. 47, pp. 261–264, 1997). Thus, thermotherapy treatment of the prostate

TABLE 1

Probability of detecting cancer on initial biopsy for different levels of PSA.

| PSA Level | Probability of Detecting Prostate Cancer on Initial Biopsy |
|---|---|
| 2 ng/ml | 1% |
| 2–4 ng/ml | 15% |
| 4–10 ng/ml | 25% |
| >10 ng/ml | >50% | is likely warranted, even if the PSA level is in the range of 0 to 4 ng/ml. Thermotherapy treatment of the prostate for PSA levels below 4 ng/ml is intended to kill the microscopic cancer cells in the prostate and keep the PSA from rising above 4 ng/ml.

Microwave radiation in the Industrial, Scientific, Medical (ISM) band 902 to 928 MHz is commonly used in commercial clinical hyperthermia systems, and is the primary frequency band considered here. It is known that the prostate is high-water content tissue and, hence, is similar to muscle tissue which is well characterized. For normal prostate tissue at 915 MHz, the average dielectric constant is 50 and the average conductivity is 1.3 S/m. The calculated loss due to attenuation of a 915 MHz plane wave propagating through prostate tissue is approximately 3 dB per cm. Prostatic intraepithelial neoplasia, also known as atypical hyperplasia and intraductal dysplasia are pre-cancers and are associated with the development of adenocarcinoma of the prostate. The neoplastic cells are assumed to be higher-water content than the surrounding normal prostate cells and will be heated faster than the normal healthy prostate cells. The normal ductal tissue in the prostate is assumed to be in the low- to medium-water content range.

The safety of employing radiofrequency (microwave) electromagnetic fields in order to treat cancer has been questioned. A comprehensive study recently concluded that there is no association between the incidence or promotion of cancer and exposure to radiofrequency electromagnetic fields in the frequency range of 3 KHz to 300 GHz (L. N. Heynick, Radiofrequency Electromagnetic Fields (RFEMF) and Cancer: A Comprehensive Review of the Literature Pertinent to Air Force Operations, AFRL-HE-BR-TR-1999-0145, United States Air Force Research Laboratory, Directed Energy Bioeffects Division, June 1999). Thus, based on this report, the Applicants realized that there is significant evidence that microwave treatment of the prostate can safely heat an apparently healthy prostate gland containing microscopic cancer cells such that no new cancer would be formed as a result of the microwave treatment.

System for Heating Prostate Tissues

FIG. 1 shows a preferred system for heating carcinomas and benign tumor cells in prostate tissues, using an adaptive energy, preferably microwave, phased array hyperthermia system with E-field and temperature feedback. In order to heat deep tissues reliably at energy frequencies, it is necessary to surround the body (prostate lobes 220) with two or more energy applicators 110, 111 (within the urethra 205 and rectum 210, respectively) controlled by an adaptive phased array algorithm. The energy applicators 110, 111 may be coherent microwave applicators. The blackened circle, indicated as focus 190, represents a central tumor or healthy tissue of the prostate 220 that is to be treated.

Focus 190 may represent cancerous conditions of the prostate including one of adenocarcinoma, carcinosarcoma, rhabdomyosarcoma, chondrosarcoma, and osteosarcoma, or pre-cancerous conditions including one of prostatic intraepithelial neoplasia, and benign prostate lesions including benign prostatic hyperplasia. In addition, the system according to the invention, can treat apparently healthy tissue in order to prevent the occurrence or re-occurrence of cancerous or benign conditions.

In the preferred embodiment, an E-field feedback probe 175 can be inserted to an appropriate depth in the tissue of prostate 220 that is to be treated. Insertion of E-field feedback probe 175 may be achieved under the guidance of an ultrasound transducer. Means for setting the initial energy phase delivered to each applicator 110, 111 includes E-field feedback signals 450 from the E-field probe 175 and computer 250 with an appropriate algorithm in order to focus the energy radiation at the inserted E-field probe 175. Preferably, the E-field probe 175 is used with an adaptive phased array fast-acceleration gradient search algorithm, as disclosed in U.S. Pat. No. 5,810,888 to Fenn, to target the energy radiation at the tumor site 190.

In addition, the system according to the invention includes means for setting the initial energy or microwave power delivered to each energy applicator, and means for monitoring the temperatures of walls of the urethra and rectum adjacent the prostate that is to be treated to ensure that those walls are not overheated. The means for monitoring urethral and rectal walls may include temperature feedback sensors 410 that are inserted non-invasively against the urethral and rectal walls (215, 216) in order to monitor the temperatures of the urethral and rectum walls adjacent the prostate tissue. Temperature feedback sensors 410 send temperature feedback signals 400 to computer 250 where signals 400 are used to adjust the relative microwave power level that is to be delivered to applicators 110, 111 to heat the tumor or tissue at focus 190.

Figure 3:
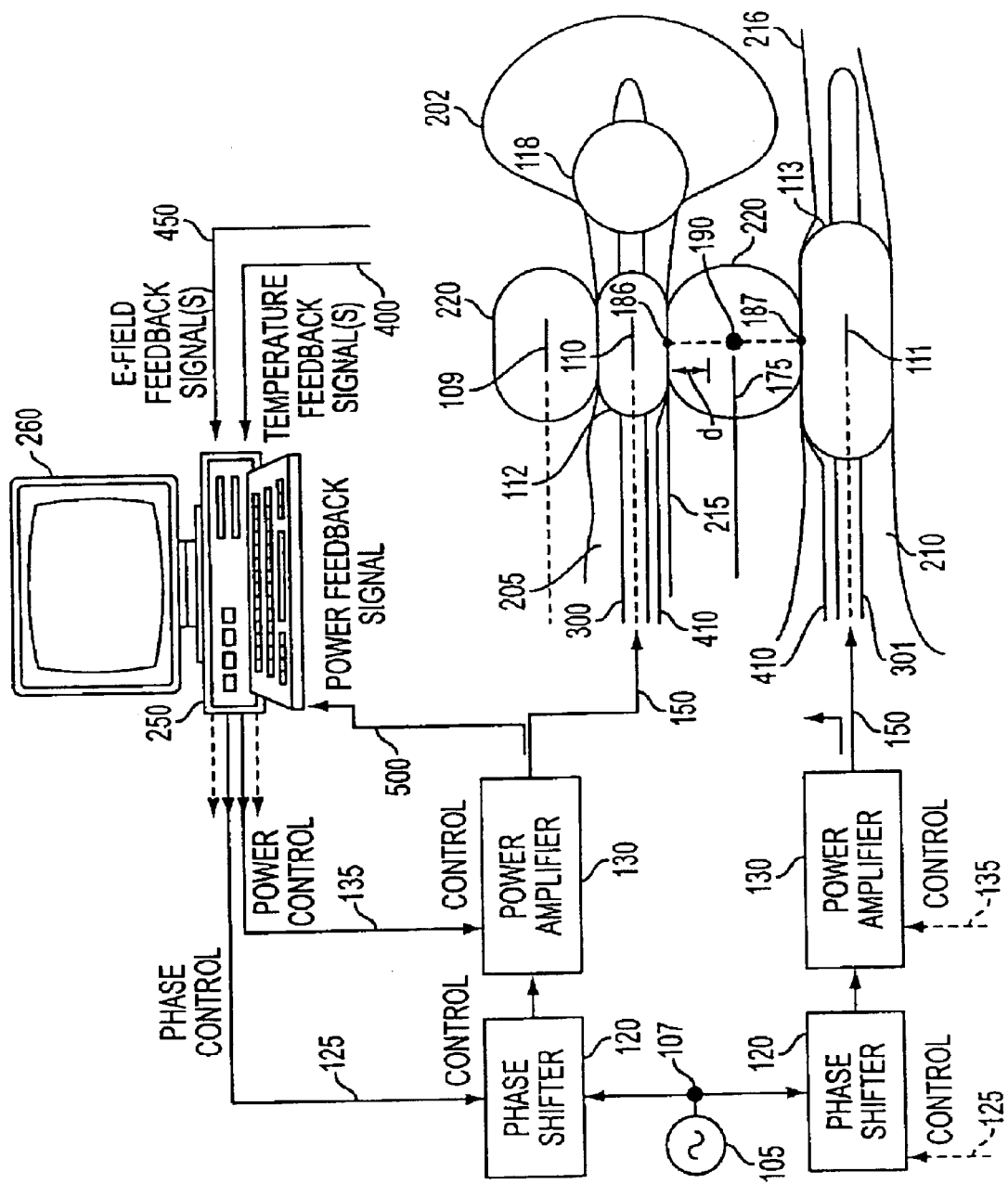
FIG. 3 shows another embodiment of the microwave therapy system of FIG. 1 employing an additional interstitial applicator.
Figure 4:
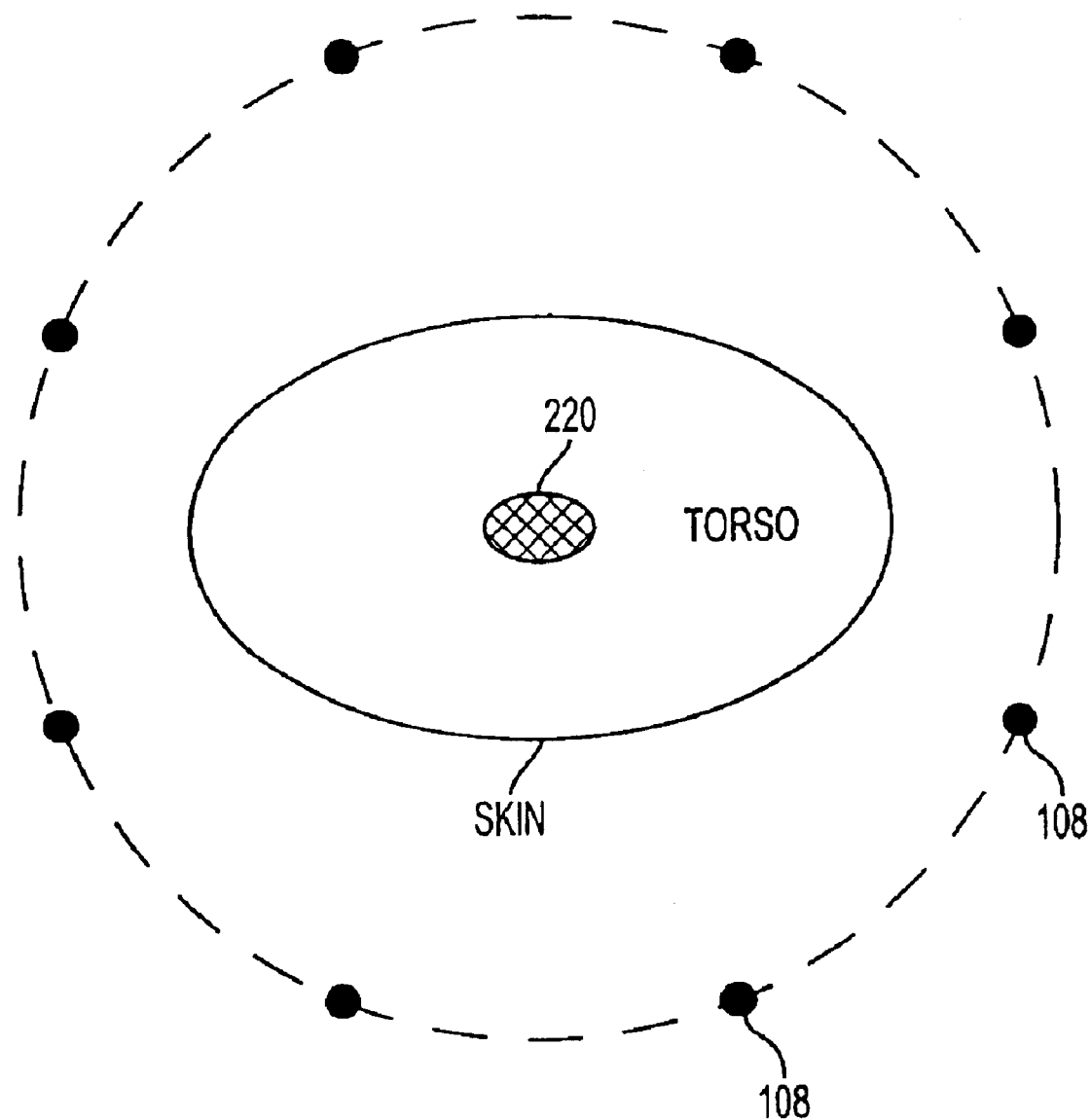
FIG. 4 illustrates a prostrate surrounded by two or more applicators outside the skin surface of the patient's body according to yet another embodiment of the invention.

Preferably, the design of the transurethral and transrectal energy applicators, which preferably are microwave applicators, is according to U.S. Pat. No. 5,007,437 to Sterzer. The transrectal applicator, in particular, may use a reflector or a phased array to direct microwave energy preferentially towards the prostate. The applicators can be noninvasive applicators such as waveguide, monopole, or dipole antennas, or interstitial applicators 109 (see FIG. 3) such as monopole or dipole antennas. In a preferred embodiment, the applicators can be driven coherently as a phased array. In addition, multiple applicators 108 surrounding the prostate 220 (see FIG. 4) that can be driven non-coherently in a multiple frequency array can be used to selectively heat the prostate tissue.

Preferably, the body or prostate 220 is compressed between two compression balloons 112, 113, which surround transurethral and transrectal applicators 110, 111, respectively. Compression balloons 112,113 can be inflated with distilled or deionized water. In the alternative, the compression balloons 112,113 can be inflated pneumatically or by other known means to inflate balloons. Compression balloons 112, 113 are made from a material such as latex that is transparent to microwaves. In addition to immobilizing the prostate tissue and fixing the positions of the applicators, prostate compression has a number of potential advantages for hyperthermia treatments. Utilization of prostate compression results in less penetration depth required to achieve deep microwave heating and reduces blood flow, which also improves the ability to heat tissue.

Injection of a local anesthetic drug such as lidocaine with ephinephrine, or anti-angiogenesis drug into the prostate tissue can be used to reduce blood flow as well. In a preferred method according to the invention, both the prostate compression technique and drug therapy for reducing blood flow in the prostate gland are used to allow rapid heating of the microscopic, malignant and benign cancer cells. This preferred method can be administered as a preventative means for cancer and BPH when PSA levels are less than 4, and for BPH when the AUA Symptom Index scores less than 13.

Compressing the prostate from the inside and outside of the prostate moves the surface of the prostate gland farther from the microwave applicator radiators, which helps to reduce superficial hot spots. In a preferred embodiment, the applicator would have a fluid filled cavity that would improve coupling of the microwave energy from the applicator to tissue to be treated. Cooling of the fluid, such as distilled or deionized water, within the transurethral and transrectal applicators or applicator balloons during hyperthermia treatments helps avoid the potential for developing hot spots in the urethra 205 and rectum 210 thereby protecting the urethral and rectal walls from overheating.

Prior to the adaptive phased array hyperthermia treatment, the prostate is compressed between compression balloons 112, 113 and a single invasive E-field feedback probe 175 is inserted within the central tissue site (focus 190) in the prostate, parallel to the polarization of the microwave applicators 110, 111. The microwave applicators 110, 111 are either monopole or dipole antenna radiators of straight or helical shape. E-field probe 175 is used to monitor the focal E-field amplitude as the phase shifters are adjusted for maximum feedback signal using an adaptive phased array gradient search algorithm. Noninvasive temperature sensors 410 monitor the urethral and rectal wall temperatures at positions 184, 185, respectively, and these signals are individually transmitted to the computer as temperature feedback signals 400.

The tips of temperature sensors 410 can be attached to the outside of the transurethral and transrectal compression balloons 112, 113 as long as the tips are thermally insulated. The thermal isolation can be achieved by mounting a thin pad (not shown) between the temperature probe and the outside surface of the balloon, from the effects of the cooling fluid contained with the compression balloons. The dual-applicator adaptive phased array of the invention together with the E-field feedback probe allows the phase shifters to be adjusted so that a concentrated E-field can be generated permitting focused heating in tissue at the appropriate depth.

Preferably, temperature sensors 410 are non-invasively inserted through the openings of the urethra 205 and rectum 210 so that the sensors 410 are in pressure contact with the respective, urethral and rectal wall. Thus, as shown in FIG. 1, two temperature feedback probe sensors 410 are located in the urethra 205 and rectum 210, respectively and produce temperature feedback signals 400. Two microwave water-cooled catheters 300, 301 with microwave applicators 110, 111, respectively, are positioned in the urethra 205 and rectum 210. Transurethral catheter 300 contains a Foley balloon 118 that is air inflated in the bladder 202 to fix the microwave applicator 110 in the correct position with respect to the target area of the prostate.

For coherent treatments, an oscillator 105 is divided at node 107 and feeds phase shifters 120. Oscillator 105 in a preferred method is a microwave energy source at approximately 915 MHz. The phase control signal 125 controls the phase of the microwave signal over the range of 0 to 360 electrical degrees. The microwave signal from each phase shifter 120 feeds into microwave power amplifiers 130. The resultant microwave signal is controlled by a computer-generated control signal 135, which sets the initial microwave power level delivered to each microwave applicator. Microwave signals 150 in the form of coherent 915 MHz microwave power is delivered by the microwave power amplifier 130 to the two applicators 110, 111 while phase shifters 120 in each channel are adjusted to maximize and focus the microwave energy at the E-field probe sensor 175 so that microwave power is maximized at the focus position 190. The treatment then begins.

In another embodiment, the means for monitoring temperature of the prostate is a temperature probe that is inserted at an appropriate depth in the prostate tissue. In this case, after the means for setting the initial relative energy phase delivered to each applicator is focussed at the E-field probe 175, the E-field probe can be removed and the temperature probe 176 can be inserted in its place temperature at an appropriate depth in the prostate tissue.

In yet another embodiment envisioned by the invention, a second temperature monitoring means, in addition to the non-invasive temperature sensors in pressure contact with the walls of the urethra and the rectum, is provided. The second temperature monitoring means is the invasive temperature probe 176 that is inserted in the prostate tissue in the same spot from which the E-field probe 175 removed.

The system and method according to the invention enable all of the treated prostate carcinomas, pre-cancerous cells, and benign lesions to be destroyed when the desired total microwave energy dose has been delivered to the microwave applicators while avoiding damage to the normal tissue of the prostate.

Figure 2:
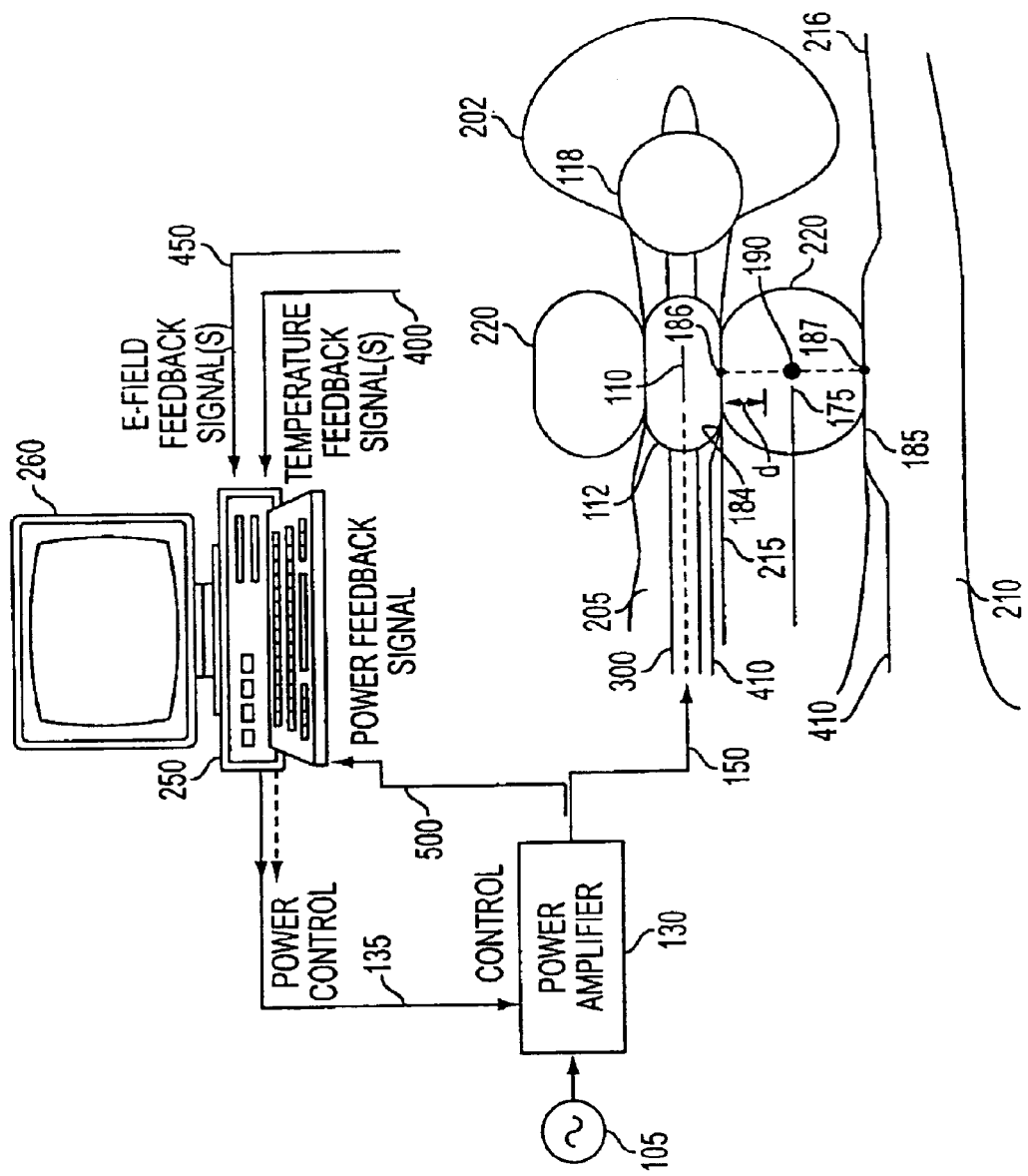
FIG. 2 shows the microwave thermotherapy system according to the invention for heating the prostate under compression from a single non-coherent transurethral applicator.

For non-coherent treatments, separate oscillators 105, which preferably operate at 915 MHz, could feed two microwave power amplifiers 130 that are computer controlled and deliver microwave power to two applicators 110, 111. For applications where a single applicator can be used, as shown in FIG. 2, a single applicator 110 located in the urethra is preferred.

During the hyperthermia treatment, the microwave signals 150 and power level delivered to each of the applicators is measured as a power feedback signal 500, which is sent to a microprocessor or computer 250 such as a PC. The power control signal of the power amplifiers 130 is adjusted either manually or automatically to control the urethra and rectum temperatures, as well as, the equivalent thermal dose delivered to the prostate tissue. The sensors 410 measure the urethral and rectal wall temperatures and the power control signal 135 is adjusted based on the sensed temperature to avoid high temperatures that could cause burns or blisters. The amount of compression realized by compression balloons 112, 113 is adjusted as necessary during treatment to provide patient comfort. Each time the prostate compression is adjusted, for coherent treatments, the phase shifters 120 are readjusted/refocused so that the E-field probe 175 receives maximum power.

According to the system according to the invention, means for monitoring the microwave energy delivered to the microwave applicators 110, 111 monitor the delivered energy/power during treatment and when the desired total microwave energy has been delivered by the microwave applicators 110, 111 to the prostate, means for terminating the treatment turn off the energy radiation to the applicators. That is, the system and method according to the invention automatically turns off the energy that is being delivered to the prostate, thereby completing the hyperthermia treatment when a desired total microwave energy dose has been delivered to the prostate 220. In a preferred embodiment, the total microwave energy dose produces a total equivalent thermal dose in prostate tumors, which is approximately between 60 minutes and 400 minutes relative to 43 degrees Celsius. The total microwave energy, since the start of the treatment, delivered to the microwave applicators is computed within computer 250 and can be displayed on the computer monitor 260 during the treatment.

As an alternate embodiment, means are provided for monitoring the microwave power level delivered to the E-field probe 175 to determine when the treatment should be terminated. According to this embodiment, the total microwave energy calculated from the E-field feedback signal 450 received by the E-field probe 175 is used to control the length of the treatment. This E-field feedback signal 450 can be useful for both coherent and non-coherent treatments. In order to determine the effectiveness of the treatment, the prostate tissue is imaged with one of x-ray and magnetic resonance imaging before and after the microwave total energy dose is administered, as well as pathological results from needle biopsy of the prostate tissues.

For coherent treatments, the single invasive E-field probe 175 can be replaced with two noninvasive E-field sensors at fixed positions 186, 187 within the urethra and rectum, respectively. The E-field sensors are inserted in the natural openings of the urethra 205, and rectum 210 and fixed in a position that is suitable to heat the tumor or healthy tissue. E-field sensors can be attached to the urethral and rectal walls at positions 186, 187, but they do not have to be in contact with the urethral and rectal walls. Ultrasound, x-rays or other known E-field monitoring device can verify the suitable E-field sensor positions. The total power measured by the two noninvasive E-field sensors is minimized (as in U.S. Pat. No. 5,810,888) by adjusting the microwave phase shifters 120, to create a focused E-field in the central portion of the prostate, or the area of the prostate to be treated.

With this embodiment, there is no risk of infection due to an inserted probe, no risk of scarring of the skin by a procedure which requires nicking the skin and inserting a probe, and no risk of spreading cancer cells as an inserted E-field probe is not used. The E-field sensors merely are fixed within the urethra and rectum and thus, do not pass through a tumor bed thereby reducing the possibility of inadvertently seeding viable cancer cells during a surgical procedure, thus reducing local recurrences of the cancer in surrounding tissues. Likewise, since both the temperature and E-field sensors can be placed in the urethra 205 and rectum 210 according to this method, the instant invention would work well when there is no defined single area in the prostate such as in the treatment of microscopic prostate disease.

Preferably, each channel (on either side of node 107) of the phased array contains an electronically-variable microwave power amplifier 130 (0 to 100 W), an electronically-variable phase shifter 120 (0 to 360 degrees), and water-cooled microwave applicators 110, 111.

While the preferred embodiment discloses microwave energy at approximately 915 MHz, the frequency of the microwave energy may be between 100 MHz and 10 GHz. The frequency of the microwave energy could be selected from the range of 902 MHz and 928 MHz. In fact, lower frequencies of energy may be used to ablate or prevent cancerous tissue.

In a preferred embodiment, the initial microwave power delivered to each applicator is between 0 and 70 Watts, preferably between 20 and 60 Watts. Over the entire treatment of the tissue, the microwave power delivered to each applicator may be adjusted over the range of 0–150 Watts to deliver the desired microwave energy dose and to avoid overheating the urethra and rectum. In addition, the relative microwave power delivered to the two microwave applicators is adjusted between −180 degrees and 180 degrees before and during the treatment to create a focussed field in the prostate tissue. Typically, more microwave power is required for non-coherent applicator treatments than for coherent applicator treatments.

In a preferred embodiment, a 0.9-mm outside-diameter (OD) invasive E-field coaxial monopole probe (semi-rigid RG-034), with the center conductor extended 1 cm, can be used as E-field probe 175 to measure the amplitude of the electric field directed to the tissue and to provide the feedback signal 450 used to determine the necessary relative phase for the electronic phase shifters prior to treatment. Coaxially-fed monopole probes of this type have been used to make accurate measurements of linearly polarized electric fields in compressed breast phantoms (Fenn et al., International Symposium on Electromagnetic Compatibility 17–19 May 1994 pp. 566–569). This linearly-polarized E-field probe is inserted within a 1.6 mm OD teflon catheter. Thermocouple probes (Physitemp Instruments, Inc., Type T copper-constantan, enclosed within a 0.6 mm OD teflon sheath) can be used to measure the local temperature in the tumor during treatment. These temperature probes have a response time of 100 ms with an accuracy of 0.1° C. Fiber-optic temperature probes may also be used.

The E-field probe 175 is used with the adaptive phased array fast-acceleration gradient search algorithm, as disclosed in U.S. Pat. No. 5,810,888 to Fenn, to target the microwave radiation at the tumor site. The temperature sensed by the invasive temperature probe 175 in the tumor could be used as a real-time feedback signal during the treatment. This feedback signal 450 could be used to control the microwave output power level of the variable power amplifiers, which set and maintain the focal temperature at the tumor site in the range of 43 to 46° C. The power and phase delivered to the two channels of the phased array are adjusted adaptively using digital-to-analog converters under computer control.

Total Microwave Energy Dose can be used to estimate the required heating time. That is, Applicants realized that a non-invasive equivalent temperature sensing means could replace the invasive temperature probes, and that the Total Microwave Energy Dose reliably could be used to control the duration of treatment. The prostate compression, as mentioned earlier, reduces blood flow, which likely eliminates the effects of blood flow on the required microwave energy for treatment, and may reduce the variation in microwave energy that can be expected in microwave treatments.

Accordingly to a preferred embodiment, the total microwave energy delivered to the waveguide applicators to determine completion of the treatment is between 25 kilo Joules and 250 kilo Joules. The total amount of microwave energy dose that would destroy any cancerous or precancerous tissue would be approximately 175 kilo Joules. But, under certain conditions, the required microwave energy dose may be as low as 25 kilo Joules.

As applicants recognized, compression of a body that results in a smaller thickness may require less microwave energy dose (compared to a compression that results in a larger thickness) for effective treatments in preventing or destroying cancerous, pre-cancerous or benign lesions. It is important to select an appropriate initial microwave power level ($P_1,P_2$) delivered to each applicator as well as the proper microwave phase between the two applicators to focus the energy at the area to be treated.

During hyperthermia treatment, it is necessary to monitor the urethral and rectal wall temperatures so that they do not rise significantly above about 41 degrees Celsius for more than several minutes. The equivalent thermal dose for the urethral and rectal wall sensors can be calculated (Sapareto, et al., International Journal of Radiation Oncology Biology Physics, Vol. 10, pp. 787–800, 1984) and can be used as a feedback signal. Typically, it is necessary to avoid delivering more than a few equivalent minutes thermal dose. Avoiding high urethral and rectal temperatures according to the invention is accomplished by adjusting the individual powers ($P_1,P_2$) delivered to the applicators during treatment either by manual or automatic computer control.

Doppler ultrasound can be used to measure blood flow in tumors and surrounding prostate tissue, before and during treatment to plan and adjust the microwave energy dose. For example, less energy dose is required when the tumor blood flow rate is reduced which can occur when the prostate is compressed and/or the tumor is heated to therapeutic temperatures. Alternatively, the water content and dielectric parameters of prostate tumor tissue from needle biopsies could be measured and used to determine, prior to the treatment, the required microwave energy dose. For example, higher water content and higher electrical conductivity in the tumor would reduce the amount of required microwave energy dose. In addition to the above variables, the size of the tumor impacts the required microwave energy dose. Larger tumors are more difficult to heat than smaller tumors and require a larger microwave energy dose. An initial treatment planning session involving a low-dose delivery of microwave energy to assess the heatability of the tumor, followed by a complete treatment at the full required microwave energy dose may be performed.

Clinical Motivation for Safety Features

In thermotherapy treatment of prostate cancer and benign prostatic hyperplasia, it is desirable to achieve therapeutic temperatures in the prostate while maintaining lower temperatures in the urethra and rectum. As the surrounding tissues in the urethra and rectum tend to be heated while microwave energy irradiates the prostate gland, methods for safely heating the prostate while protecting the surrounding healthy tissues need to be developed.

In FIGS. 1–4, following application of microwave thermotherapy, microwave power control signals 135 command at least one of the microwave power amplifier 130 for the transurethral applicator and/or the microwave amplifier 130 for the transrectal applicator to turn off and at least one of a transurethral balloon 112 and a transrectal balloon 113 maintain pressure on the prostate gland to reduce blood flow thereby trapping heat to accumulate additional thermal dose. This safety embodiment can be used for heat-alone prostate treatments or when thermotherapy is used with chemotherapy or to release chemotherapy from thermosensitive liposomes as described in U.S. Pat. No. 5,810,888 to Fenn. The blood flow rate can be measured and displayed during prostate compression by doppler ultrasound imaging in order to verify and adjust the blood flow rate in the prostate by varying the amount of prostate compression.

In chemotherapy, thermosensitive liposome delivered chemotherapy, or gene therapy for prostate cancer it is desirable to deliver as much drug as possible to the tissue to be treated of a patient. The desired therapeutic agent in the form of chemotherapy, thermosensitive liposome delivered chemotherapy, gene therapy, or other agent is infused into the blood stream of a patient. The compression of the transurethral and/or transrectal balloon catheters may be modulated so that the blood flow in the prostate tissue can be adjusted. The blood flow in the prostate is reduced by increasing pressure of the compression balloons in the urethra and/or rectum. This reduction in blood flow in the prostate means that the infused therapeutic agent will spend more time within the prostate tissue, potentially increasing the therapeutic value. Further, if the therapeutic agent spends more time within the prostatic blood vessels, there is an increased likelihood that the therapeutic agent will extravasate (permeate or leak) from the blood vessels into the prostatic tissues to reach the prostate cancer cells. Consequently, the compression of the prostate may increase the amount of therapeutic agent delivered to the prostate while decreasing the amount of therapeutic agent released into normal healthy surrounding tissues.

The desired sequence of balloon compression of the prostate is as follows. After chemotherapy, thermosensitive liposome delivered chemotherapy, gene therapy, or another agent is infused into the patient's bloodstream, the prostate gland is compressed by at least one of the transurethral and transrectal balloon catheters for a period of between 1 minute and 10 minutes. Then, at least one of the transurethral and transrectal balloons is deflated to allow normal blood flow into the prostate for a period of less than 1 minute to allow the therapeutic agent to enter the prostatic bloodstream, but without substantially lowering the temperature of the prostate. And then the prostate gland is compressed again for a period of between 1 minute and 10 minutes to reduce the blood flow thereby trapping the therapeutic agent within the prostate gland. The above described process of inflation and deflation of the balloon catheter(s) is repeated until the desired amount of therapeutic agent is delivered to the prostate while the prostate is heated.

In a preferred embodiment, the chemotherapy agent is Doxorubicin (Adriamycin). In another preferred embodiment, the thermosensitive liposome formulation is as described in U.S. Pat. No. 6,200,598 to Needham.

Applicants envision that doppler ultrasound imaging may be employed to determine the blood flow rate of the tumor. That is, doppler ultrasound imaging can measure the tumor blood flow rate with or without compression of the prostate and use these measurements as feedback during the treatment in order to assess any damage to the prostate tumor vasculature.

Simplified Microwave Radiation Theory

Microwave energy from hyperthermia applicators, in the near field of a body, radiates as a spherical wave with the electric-field amplitude varying, in part, as the inverse of the radial distance r from the applicator. Additionally, the amplitude decays as an exponential function of the product of the attenuation constant $\alpha$ of the body tissue and the distance d traversed (or depth) within the body as indicated in FIG. 1. The electric-field phase varies linearly with distance according to the product of the phase propagation constant $\beta$ and distance d. For simplicity, dual-opposing applicators are analyzed here under the assumption that the applicator radiation is approximated by a plane wave. Mathematically, the plane-wave electric field versus depth in tissue is given by $E(d)=E_o \exp(-\alpha d) \exp(-i\beta d)$, where $E_o$ is the surface electric field (in general represented by an amplitude and phase angle), and i is the imaginary number (Field and Hand, An Introduction to the Practical Aspects of Clinical Hyperthermia, Taylor & Francis, New York p. 263, 1990).

Plane-wave electromagnetic energy, at the microwave frequency of 915 MHz, attenuates at a rate of about 3 dB per cm in high-water content tissue, such as prostate tissue. Thus, a single radiating applicator has a significant fraction of its microwave energy absorbed by intervening superficial body tissue compared to the energy that irradiates deep tissue, likely creating a hot spot in superficial tissue. Since surface cooling with either air or water protects tissue only to a maximum depth of about 0.25 to 0.5 cm, in order to avoid hot spots, it is necessary to introduce a second phase-coherent applicator, having the same microwave radiation amplitude as the first applicator. The second phase-coherent applicator can theoretically increase the power (and hence the energy) delivered to deep tissue by a factor of four compared to a single applicator (Field and Hand, p. 290, 1990).

The phase characteristics of the electromagnetic radiation from two or more applicators (known as a phased array) can have a pronounced affect on the distribution of power delivered to different tissues. The relative specific absorption rate (SAR) in homogeneous tissue is approximated by the square of the electric-field amplitude $|E|^2$. The SAR is proportional to the rise in temperature over a given time interval. A simplified case, homogeneous prostate tissue, in which the microwave radiation is focused at a central tissue site, is described in detail below. As described in an article by Fenn et al., International Symposium on Electromagnetic Compatibility, Sendai, Japan, Vol. 10, No. 2, May 17–19, 1994, pp. 566–569, the effects of multiple microwave signal reflections within the phantom can be ignored.

The wavelength in homogeneous normal prostate tissue (with approximate dielectric constant 50 and electrical conductivity 1.3 S/m) is approximately 4.5 cm at 915 MHz, and the microwave loss is 3 dB/cm. The attenuation constant a is 0.34 radians/cm and the propagation constant $\beta$ is 1.4 radians/cm (or 80 degrees/cm). (For a compressed prostate thickness of 2.25 cm, the electric field of a single applicator radiating on the left side is $E_o$ at the surface of the prostate, $-i0.7E_o$ (where i represents a 90-degree phase shift) at the central position (1.125 cm deep), and $-0.5E_o$ at the right surface. Combining two phase coherent applicators yields an electric-field value of $0.5E_o$ on both surfaces and $-i1.4E_o$ at the central position (1.125 cm depth). Thus, for the compressed prostate, by squaring the above coherent E-fields to compute SAR, there is a significantly lower SAR at the surface, by about a factor of 2.0 compared to the central SAR. The 180-degree phase shift experienced by the microwave field transmitted through 2.25 cm of prostate tissue, partly cancels or nulls the field entering the tissue with 0-degree phase shift. Due to destructive interference of the microwaves away from the central focus lower temperatures in the superficial prostate tissues would be expected. Measurement and enforcement of lower SAR on the opposing surfaces effectively focuses the microwave energy deep in the prostate. In cases where it is desirable to radiate the superficial or peripheral zone prostate tissues more strongly, the compression thickness can be larger than 2.25 cm so that the propagating wave phase delay is longer and the two waves do not cancel at the surface, or only one of the transurethral or transrectal applicators (especially the transrectal applicator) can be used to heat the prostate.

Repeating the above calculation, but now for non-coherent applicators, for a compressed prostate thickness of 2.25 cm, the electric field of a single applicator radiating on the left side is $E_o$ at the surface of the prostate, $-i0.7E_o$ (where i represents a 90-degree phase shift) at the central position (1.125 cm deep), and $-0.5E_o$ at the right surface. Combining two applicators non-coherently, by squaring the individual E-fields and adding them, yields a SAR value of $1.5E_o^2$ on both surfaces and $0.98\ E_o^2$ at the central position (1.125 cm depth). Thus, for the compressed prostate, by squaring the above non-coherent E-fields to compute SAR, there is a significantly higher SAR at the surface, by about a factor of 1.5 compared to the central SAR. For this reason, it is more difficult to heat deep prostate tissue with the non-coherent array compared to the coherent array. However, as mentioned earlier, for prostate cancer treatment some of the prostate cancer cells can be located close to the rectum and non-coherent treatment may provide adequate heating.

The adaptive phased array system according to the invention uses two microwave channels, fed by a common oscillator 105, containing two electronically adjustable phase shifters 120 to focus the microwave energy at an E-field feedback probe 175. This inventive adaptive phased array system has significant advantage over a non-adaptive phased array. A non-adaptive phased array with two channels could, in theory, produce a null, a maximum, or an intermediate value of E-field depending on whether the two waves are 180 degrees out-of-phase, completely in-phase, or partly out-of-phase, respectively. That is, the microwave phase delivered to the microwave applicators, according to the invention, can be adjusted between −180 degrees and 180 degrees before and during the treatment to create a focused field in the prostate tissue.

The adaptive phased array according to the invention automatically focuses the E-field in the presence of all scattering structures in the tissue. Thus, the adaptive phased array according to the invention should provide more reliable deep focused heating compared to manually adjusted or pre-treatment planning controlled phased arrays as described in U.S. Pat. No. 4,589,423 to Turner. Furthermore, the adaptive phased array system according to the invention does not use an invasive temperature probe, which could scatter or alter the E-field at the tumor site.

Calculation of Microwave Energy

Electrical energy consumption is commonly expressed in units of kilowatt hours. Mathematically, the expression for the microwave energy W delivered by an applicator is given by (Vitrogan, Elements of Electric and Magnetic Circuits, Rinehart Press, San Francisco, pp. 31–34, 1971):

$$W = \Delta t\ \Sigma P_i. \tag{1}$$

In the above equation, $\Delta t$ represents the constant intervals (in seconds) in which microwave power is measured and the summation $\Sigma$ is over the complete treatment interval with the power (in Watts) in the ith interval denoted by $P_i$.

The microwave energy W has units of watt-seconds, which is also designated as Joules. For example, in three consecutive 60-second intervals if the microwave power is 30 watts, 50 watts, 60 watts, respectively, the total microwave energy delivered in 180 seconds is calculated as W=60 (30+50+60)=8,400 watt-seconds=8,400 Joules=8.4 kJ.

To understand better the focused energy per unit time W' (where ' denotes prime) deposited at a central position in homogeneous prostate tissue of varying thickness (denoted by D) by dual-opposing applicators, consider the following calculation for coherent treatments. Let $P_1$ and $P_2$ be the power delivered to the two applicators, respectively. The electric field radiated by each applicator is proportional to the square root of the power delivered to the applicator. Assuming symmetry, the radiated fields are in-phase at the central focused position from the two applicators. Assuming equal power from each applicator, that is, $P_1=P_2=P$, and plane wave illumination, then the focused energy per unit time at the central depth is expressed as $$W'(D) = |E|^2 = 4P\ \exp(-\alpha D). \tag{2}$$

Calculation of Equivalent Thermal Dose

The cumulative or total equivalent thermal dose relative to 43 degrees Celsius is calculated as a summation (Sapareto, et al., International Journal of Radiation Oncology Biology Physics, Vol. 10, pp. 787–800, 1984):

$$t_{43}°\ \text{C. equivalent minutes} = \Delta t\ \Sigma R^{(43°-T)}. \tag{3}$$

where $\Sigma$ is the summation over a series of temperature measurements during the treatment, T is the series of temperature measurements $(T_1, T_2, T_3, \ldots)$, $\Delta t$ is the constant interval of time (units of seconds and converted to minutes) between measurements, R is equal to 0.5 if T>43° C. and R is equal to 0.25 if T<43° C. The equivalent thermal dose calculation is useful for assessing any possible heat damage to the prostate tissues, urethra and rectum.

Equivalents

While this invention has been particularly shown and described with reference to preferred embodiments thereof, it will be understood by those skilled in the art that various changes in form and details may be made therein without departing from the spirit and scope of the invention as defined by the appended claims. For instance, although the hyperthermia system described herein is with respect to the treatment of prostate carcinomas and benign prostate lesions, the invention is applicable to the treatment of other types of cancers such as breast, liver, lung, and ovarian. In addition to the disclosed preferred embodiments, it is understood that the methods disclosed here can be applied to microwave, radiofrequency, or ultrasound thermotherapy treatments of other appendages and portions of the human body, such as legs and arms and the torso that can be compressed with a balloon cuff (for example, a blood pressure cuff) or other device. It is also understood that larger or smaller numbers of array antenna applicators, or single antenna applicators such as an implant, or transurethral or transrectal applicator, may be used with similar results. Some of the methods and techniques described herein are also applicable to ultrasound hyperthermia system particularly the use of energy dose for feedback control. The system according to the invention can be used to enhance radiation therapy or for targeted drug delivery and/or targeted gene delivery using thermosensitive liposomes or for targeted gene therapy. The invention is also applicable to non-medical hyperthermia system, such as those used for industrial heating.

We claim:

1. A method for treating tissue of the prostate comprising the steps of:

heating targeted prostate tissue via energy to a temperature so that the urethral and rectal walls near the prostate do not rise significantly above 41° C. for more than several minutes; and compressing the prostate following the application of the energy, the energy being selected from the group comprising microwave, ultrasound, laser and energy via a fluid to reduce prostatic blood flow in order to accumulate added thermal dose in the targeted prostate tissue.

2. The method for treating the prostate according to claim 1, wherein the application of energy is achieved with a single applicator, said applicator being selected from the group comprising an implant, a transurethral applicator and a transrectal applicator.

3. The method for treating the prostate according to claim 1, wherein the compression step is achieved by inflating a balloon selected from the group comprising a transurethral catheter balloon, a transrectal balloon, and a combination of a transurethral catheter balloon and transrectal balloon.

4. The method for treating the prostate according to claim 3, further comprising the step of using real-time feedback from a doppler ultrasound velocity imaging system to adjust and verify the amount of prostate compression as a result of the transurethral and/or transrectal balloon inflation.

5. A method for safely administering thermotherapy, comprising the steps of:

applying energy selected from the group comprising microwave energy, ultrasound energy, laser energy and energy via a fluid;

following the application of energy selected from the group comprising microwave energy, ultrasound energy, laser energy and energy via a fluid, compressing at least one of an organ and an appendage to be treated by using one of a balloon catheter and a balloon cuff to reduce organ or appendage blood flow therein; and applying therapy selected from the group comprising chemotherapy, gene therapy, thermosensitive liposomes containing chemotherapy, and radiation therapy in combination with the compression in order to treat cancer and/or a benign condition of the organ and/or appendage.

6. The method for safely administering thermotherapy according to claim 5, wherein the balloon catheter is selected from the group comprising a transurethral balloon catheter, a transrectal balloon catheter, and a combination of the transurethral balloon catheter and a transrectal balloon catheter.

7. The method for safely administering thermotherapy according to claim 6, wherein the organ being treated is the prostate and a balloon catheter is employed to compress the catheter, and further comprising the steps of adjusting the amount of prostate compression and verifying the amount of prostate compression as a result of the transurethral and/or transrectal balloon catheter.

8. The method for safely administering thermotherapy according to claim 7, wherein the steps of adjusting and verifying are achieved using real-time feedback from a doppler ultrasound velocity imaging system.

9. The method for safely administering thermotherapy according to claim 5, wherein the organ is the prostate, a balloon catheter is used to compress the prostate and the compressing step of the prostate occurs after therapy selected from the group comprising chemotherapy, thermosensitive liposomes containing chemotherapy, and radiation therapy is infused into the bloodstream of a patient to deliver a therapeutic agent; said compressing step including inflating the balloon catheter thereby compressing the prostate gland for a first time period between approximately 1 minute to approximately 10 minutes, and then, after the compression of the first time period, deflating the balloon catheter to allow unrestricted blood flow into the prostate for a second time period of less than approximately 1 minute.

10. The method for safely administering thermotherapy according to claim 9, wherein the process of inflating and deflating the balloon catheter is repeated until the desired amount of therapeutic agent is delivered to the prostate.

11. The method for safely administering thermotherapy according to claim 5, wherein an appendage is to be compressed and treated for cancer and/or a benign condition.

12. The method for safely administering thermotherapy according to claim 11, wherein the appendage is one of a arm, leg or torso.

13. A method for effectively delivering therapy selected from the group comprising chemotherapy, thermosensitive liposomes containing chemotherapy, and gene therapy comprising the steps of applying one of chemotherapy, thermosensitive liposomes containing chemotherapy, and gene therapy to an organ or an appendage; and then modulating inflation and deflation of one of a balloon catheter and a balloon cuff about the organ or appendage to compress the organ or appendage to vary the blood flow therein.

14. The method for effectively delivering therapy according to claim 13, further comprising the step of heating tissue of the organ or tissue with energy selected from the group, comprising microwave, ultrasound, radiofrequency, and laser energy and wherein the modulating compression of the organ or appendage and thermotherapy together increase the medicinal effects of one of the delivered chemotherapy, thermosensitive liposomes containing chemotherapy, and gene therapy.

15. The method for effectively delivering therapy according to claim 14, wherein the organ being treated is the prostate.

16. The method for effectively delivering therapy according to claim 14, wherein the appendage being treated is one of an arm, a leg and a torso.

17. A method for effectively delivering liposomes containing chemotherapy to a prostate to be treated comprising the steps of applying energy selected from the group comprising microwave energy, ultrasound energy, laser energy and energy via a fluid to the prostate to be treated; and time-modulating balloon catheter compression of the prostate gland to reduce blood flow in the prostate thereby reducing blood flow and providing more time for liposomes containing chemotherapy to deliver chemotherapy to the prostate.

18. The method for effectively delivering liposomes according to claim 17, wherein the step of time-modulating the balloon catheter compression uses real-time feedback from a doppler ultrasound velocity imaging system to adjust and verify the amount of prostate compression.

19. The method for effectively delivering liposomes according to claim 17, wherein the compression step is achieved by inflating a balloon selected from the group comprising a transurethral catheter balloon, a transrectal balloon, and a combination of a transurethral catheter balloon and a transrectal balloon.

20. A method for early treatment of cancerous, pre-cancerous, or benign conditions of a prostate by irradiation of the prostate, comprising the steps of:
- a) Determining one of the prostate specific antigen (PSA) level and the American Urological Association (AUA) Symptom Index of a patient;
- b) compressing the prostate of the patient;
- c) Heating the patient's compressed prostate with focused microwave energy when either the PSA level is less than 4.0 ng/ml or the AUA index is less than 13 to reduce the production of PSA in the prostate; and
- d) Following the application of energy selected from the group comprising microwave energy, ultrasound energy, laser energy and energy via a fluid, compressing the prostate to reduce prostatic blood flow in order to accumulate added thermal dose in the prostate.

* * * * *